United States Patent [19]

Dean

[11] Patent Number: 5,552,525
[45] Date of Patent: Sep. 3, 1996

[54] TECHNETIUM-99M LABELED PEPTIDES FOR IMAGING INFLAMMATION

[75] Inventor: Richard T. Dean, Bedford, N.H.

[73] Assignee: Diatech Inc., Londonderry, N.H.

[21] Appl. No.: 19,864

[22] Filed: Feb. 19, 1993

Related U.S. Application Data

[63] Continuation-in-part of Ser. No. 653,012, Feb. 8, 1991, abandoned.

[51] Int. Cl.$^6$ .......................... A61K 38/00; A61K 51/00; C07K 2/00
[52] U.S. Cl. .......................... 530/326; 530/300; 530/322; 424/9.3; 424/9.35; 424/9.4; 424/9.43; 424/9.6
[58] Field of Search .................... 530/326, 382, 530/402, 300, 322; 424/1.11, 1.69, 1.73, 1.1, 9.3, 9.35, 9.4, 9.43, 9.6

[56] References Cited

U.S. PATENT DOCUMENTS

| | | | |
|---|---|---|---|
| 4,057,617 | 11/1977 | Abramovici et al. | 424/1.11 |
| 4,385,046 | 5/1983 | Milbrath et al. | 424/1.11 |
| 4,444,690 | 4/1984 | Fritzberg | 530/326 |
| 4,935,223 | 6/1990 | Phillips | 424/1.11 |
| 4,986,979 | 1/1991 | Morgan, Jr. et al. | 424/1.11 |
| 5,198,424 | 3/1993 | McEver | 530/326 |
| 5,266,562 | 11/1993 | Mukherjee et al. | 530/326 |
| 5,308,603 | 5/1994 | Thakur | 530/402 |
| 5,376,356 | 12/1994 | Morgan, Jr. | 424/1.41 |

FOREIGN PATENT DOCUMENTS

| | | |
|---|---|---|
| 0301458 | 2/1989 | European Pat. Off. . |
| 0398143 | 11/1990 | European Pat. Off. . |
| WO9010463 | 9/1990 | WIPO . |

OTHER PUBLICATIONS

Takefumi et al, Molecular & Cellular Biology, pp. 898–904, (1987).
Deuel et al., "Amino acid sequence of human platelet factor 4", 1977, Proc. Natl. Acad. Sci. USA 74:2256–2258.
Niedel and Cuatrecasas, 1980, "Formyl Peptide Chemotactic Receptors of Leukocytes and Macrophages", in Curr. Top. Cell. Reg. 17: 137–170.
Deuel et al., "Platelet factor 4 is chemotactic for neutrophils and monocytes", 1981, Proc. Natl. Acad. Sci. USA 78:4584–4587.
Zoghbi et al., "Selective cell labeling: A potential radioactive agent for labeling human neutrophils", 1981, J. Nucl. Med. 22:32 (Abst).
Jiang et al., "Localization of abscess with an iodinated synthetic chemotactic peptide", 1982, Nuklearmedizin 21:110–113.
Osterman et al., "The carboxyl–terminal tridecapeptide of platelet factor 4 is a potent chemotactic agent for monocytes", 1982, Biochem. Biophys. Res. Comm. 107:130–135.
Holt & Niewiarowski, "Biochemistry of α–granule proteins", 1985, Sem. Hematol. 22:151–163.
Goldman et al., "Inhibition of human neutrophil receptor–mediated uptake of N–formyl–mey–leu–phe by platelet factor 4(59–70)", 1985, Immunol. 54:163–171.
Loscalzo et al., "The interaction of platelet factor 4 and glycosaminoglycans", 1985, Arch. Biochem. Biophys. 240:446–455.
Bebawy et al., "In vitro effects of platelet factor 4 on normal human neutrophil functions", 1986, J. Leukocyte Biol. 39:423–434.
Wilkinson, "Chemotactic factors: An overview", 1988, Meth. Enzymol. 162: 127–132.
Vorne et al., "Technetium–99m HM–PAO–labeled leukocytes in detection of inflammatory lesions: Comparison with gallium–67 citrate", 1989, J. Nucl. Med. 30: 1332–1336.
LaMuraglia et al., "Utility of the indium 111–labeled human immunoglobulin G scan for the detection of focal vascular graft infection", 1989, J. Vasc. Surg. 10: 20–28.
Maione et al., "Inhibition of angiogenesis by recombinant human platelet factor 4 and related peptides", 1989, Science 247:77–79.
Lind et al., "Immunoscintigraphy of inflammatory processes with a technietium–99m–labeled monoclonal antigranulocyte antibody (MAb BW 250183)", 1990, J. Nucl. Med. 31: 417–423.
Fischman et al., "Imaging focal sites of bacterial infection in rats with indium–111–labeled chemotactic peptide analogs", 1991, J. Nucl. Med. 32: 483–491.

*Primary Examiner*—John Kight
*Assistant Examiner*—Louise Leary
*Attorney, Agent, or Firm*—Banner & Allegretti, Ltd.

[57] ABSTRACT

This invention relates to reagents, radiolabeled reagents and methods for producing such reagents and radiolabeled reagents. Specifically, the invention relates to technetium-99m (Tc-99m) labeled peptides that specifically bind to inflammatory sites in vivo, methods and kits for making such peptides, and methods for using such peptides to image sites of infection and inflammation in a mammalian body.

27 Claims, No Drawings

TECHNETIUM-99M LABELED PEPTIDES FOR IMAGING INFLAMMATION

This is a continuation-in-part of U.S. patent application Ser. No. 07/653,012, filed Feb. 8, 1991, now abandoned.

BACKGROUND OF THE INVENTION

1. Field of the Invention

This invention relates to radiodiagnostic reagents and peptides, methods of using these radiodiagnostic reagents and methods for producing such labeled radiodiagnostic agents. Specifically, the invention relates to technetium-99m (Tc-99m) labeled reagents, methods and kits for making such reagents, and methods for using such reagents to image sites of infection and inflammation in a mammalian body.

2. Description of the Prior Art

There is a clinical need to be able to determine the location and/or extent of sites of focal or localized infection. In a substantial number of cases conventional methods of diagnosis (such as physical examination, x-ray, CT and ultrasonography) fail to identify such sites (e.g., an abscess). Although biopsy may be resorted to, it is preferable to avoid such invasive procedures, at least until they are diagnostically appropriate to identify the pathogen responsible for an abscess at a known location. Identifying the site of such "occult'" infection is important because rapid localization and identification of the problem is critical to effective therapeutic intervention.

In the field of nuclear medicine, certain pathological conditions can be localized or the extent of such conditions determined by imaging the internal distribution of administered radioactively-labeled tracer compounds (i.e. radiotracers or radiopharmaceuticals) that accumulate specifically at the pathological site. A variety of radionuclides are known to be useful for radioimaging, including $^{67}$Ga, $^{99m}$Tc (Tc-99m), $^{111}$In, $^{123}$I, $^{125}$I, $^{169}$Yb and $^{186}$Re.

However, an abscess may be caused by any one of many possible pathogens, so that a radiotracer specific for a particular pathogen would have limited scope. On the other hand, infection is almost invariably accompanied by inflammation, which is a general response of the body to tissue injury. Therefore, a radiotracer specific for sites of inflammation would be expected to be useful in localizing sites of infection caused by any pathogen, as well as being useful for localizing other inflammatory sites.

One of the main phenomena associated with inflammation is the localization of leukocytes (white blood cells), usually monocytes and neutrophils, at the site of inflammation. A radiotracer specific for leukocytes would be useful in detecting leukocytes at the site of a localized infection. Currently approved nuclear medicine procedures for imaging sites of infection use either indium-111 labeled leukocytes ($^{111}$In-WBC) (see, e.g. Peters, 1992, J. Nucl. Med. 33: 65–67) or gallium-67 ($^{67}$Ca) citrate (see, e.g. Ebright et al., 1982, Arch. Int. Med. 142: 246–254). A major disadvantage of using $^{111}$In-labeled WBCs is that the preparation of the radiotracer requires a number of technical steps: sterile removal of autologous blood, sterile isolation of the leukocytes from the blood, sterile labeling of the leukocytes using conditions that do not damage the cells (since damaged WBC are taken up by the reticuloendothelial system when re-injected) and sterile return (re-injection) of the (now labeled) leukocytes to the patient. Furthermore, a delay of 12 to 48 hours between injection and imaging may be required to obtain optimum imaging. While Tc-99m labeled leukocytes have been used to shorten this delay period (see, e.g. Vorne et al., 1989, J. Nucl. Med. 30: 1332–1336), ex-corporeal labeling is still required. A preferred radiotracer would be one that does not require removal and manipulation of autologous blood components.

Alternatively, $^{67}$Ga-citrate can be administered by intravenous injection. However, this compound is not specific for sites of infection or inflammation. Moreover, a delay of up to 72 hours is often required between injection of the radiotracer and imaging. In addition, the γ-(gamma) emissions energies of $^{67}$Ga are not well suited to conventional gamma cameras.

Radiolabeled monoclonal and polyclonal antibodies raised against human leukocytes (including monocytes, neutrophils, granulocytes and other cell types) have been developed. Tc-99m labeled antigranulocyte monoclonal antibodies (see, e.g. Lind et al., 1990, J. Nucl. Med. 31: 417–473) and $^{111}$In-labeled non-specific human immunoglobulin (see, e.g. LaMuraglia et al., 1989, J. Vasc. Surg. 10: 20–28) have been tested for the detection of inflammation secondary to infection. $^{111}$In-labeled IgG shares the disadvantages of $^{111}$In-labeled WBC, in that 24–48 hours are required between injection and optimal imaging. In addition, all radiolabeled antibodies are difficult to produce and face protracted approval procedures, as they are routinely classified as biologics by regulatory agencies.

Small readily synthesized molecules are preferred as routinely-used radiopharmaceuticals. There is clearly a need for small synthetic molecules that can be directly injected into a patient and will image sites of infection and inflammation by localizing at sites where leukocytes have accumulated. One kind of small, readily synthesized molecule useful in such applications are peptides.

The sensitivity of imaging methods using radioactively-labeled peptides is much higher than other techniques known in the art, since the specific binding of the radioactive peptide concentrates the radioactive signal over the area of interest, for example, an inflammatory site. In addition, methods for achieving high-yield chemical synthesis of small peptides is well known in the art.

One class of peptides known to bind to leukocytes are chemotactic peptides that cause leukocytes to move up a peptide concentration gradient (see Wilkinson, 1988, Meth. Enzymol. 162: 127–132). These compounds bind to receptors on the surface of leukocytes with very high affinity. These peptides are derived from a number of sources, including complement factors, bacteria, tuftsin, elastin, fibrinopeptide B, fibrinogen Bβ, platelet factor 4 and others. Small synthetic peptides derived from these chemotactic compounds and radiolabeled would be very useful as radiotracers for imaging sites of inflammation in vivo.

Radiolabeled peptides have been reported in the prior art.

Zoghbi et al., 1981, J. Nucl. Med. 22: 32 (Abst) disclose formyl peptide chemotactic factors (fMLF) derived from bacteria coupled to $^{111}$In-labeled transferrin.

Jiang et al., 1982, Nuklearmedizin 21: 110–113 disclose a chemotactic formylated peptide (fMLF) radiolabeled with $^{125}$I.

Fischman et al., 1991, J. Nucl. Med. 32: 482–491 relates to chemotactic formyl peptide (fMLF)—$^{111}$In-labeled DTPA conjugates.

EPC 90108734.6 relates to chemotactic formyl peptide (fMLF)—$^{111}$In-labeled DTPA conjugates.

U.S. Pat. No. 4,986,979 relates to the use of radiolabeled chemotactic formyl peptides (fMLF) to radiolabel leukocytes ex-corporeally via a photoaffinity label.

PCT WO90/10463 relates to the use of radiolabeled chemotactic formyl peptides (fMLF) to radiolabel leukocytes ex-corporeally via a photoaffinity label.

The use of labeled formyl-methionyl-leucyl-phenylalanyl (fMLF) peptides known in the aforementioned art suffers from the serious drawback that this peptide causes superoxide release from neutrophils (Niedel and Cuatrecasas, 1980, *Formyl Peptide Chemotactic Receptors of Leukocytes and Macrophages*, in Curr. Top. Cell. Reg. 17: 137–170) and at sufficient doses can cause leukocytopenia (Jiang et al., 1982, Nuklearmed. 21: 110–113).

Platelet factor 4 is a naturally-occurring chemotactic peptide, consisting of 70 amino acids and known in the prior art to bind to neutrophils and monocytes, cell types known to be associated with sites of inflammation and infection in vivo.

Thorbecke & Zucker, 1989, European Patent Application No. 88111962.2 disclose compositions and methods for modulating immune responses comprising administering an immunomodulating amount of platelet factor 4 or peptides derived therefrom.

Deuel et al., 1977, Proc. Natl. Acad. Sci. USA 74: 2256–2258 disclose the amino acid sequence of human platelet factor 4.

Deuel et al., 1981, Proc. Natl. Acad. Sci. USA 78: 4584–4587 disclose that platelet factor 4 is chemotactic for neutrophils and monocytes in vitro.

Osterman et al., 1982, Biochem. Biophys. Res. Comm. 107: 130–135 disclose that the carboxyl-terminal tridecapeptide of platelet factor 4 has chemotactic properties.

Holt & Niewiarowski, 1985, Sem. Hematol. 22: 151–163 provide a review of the biochemistry of platelet α-granule proteins, including platelet factor 4.

Goldman et al., 1985, Immunol. 54: 163–171 reveal that fMLF receptor-mediated uptake is inhibited in human neutrophils by platelet factor 4 and a carboxyl-terminal dodecapeptide thereof.

Loscalzo et al., 1985, Arch. Biochem. Biophys. 240: 446–455 describe the biochemical interaction between platelet factor 4 and glycosaminoglycans such as heparin.

Bebawy et al., 1986, J. Leukocyte Biol. 39: 423–434 describe the platelet factor 4-mediated chemotactic response of neutrophils in vitro.

Maione et al., 1989, Science 247: 77–79 disclose that angiogenesis is inhibited by recombinant human platelet factor 4 and peptide fragments thereof.

The use of chelating agents for radiolabeling polypeptides, and methods for labeling peptides and polypeptides with Tc-99m are known in the prior art and are disclosed in U.S. patent application Ser. Nos. 07/653,012 filed Feb. 8, 1991, now abandoned; 07/807,062 filed Nov. 27, 1992 now U.S. Pat. No. 5,443,815; 07/851,074 filed Mar. 13, 1992 now abandoned; 07/886,752 filed May 21, 1992 now abandoned, 07/893,981 filed Jun. 5, 1992 now U.S. Pat. No. 5,508,020; 07/955,466 filed Oct. 2, 1992 now abandoned; and copending application Ser. Nos. 07/871,282 filed Apr. 30, 1992 and 07/902,935 filed Jun. 23, 1992, which are hereby incorporated by reference.

SUMMARY OF THE INVENTION

The present invention provides scintigraphic imaging reagents that are radioactively-labeled peptides. The reagents of the invention are comprised of peptides that specifically bind to sites of inflammation in vivo and are covalently linked to a radioisotope complexing group wherein the complexing group binds a radioisotope.

The invention provides reagents that bind to sites of inflammation in vivo, radiolabeled complexes of such reagents with technetium-99m, methods for preparing such complexes, methods for using such radiolabeled complexes for imaging sites of infection and inflammation within a mammalian body, and methods for preparing the inflammation-imaging reagents of the invention.

In a first aspect of the present invention, radiolabeled peptides are provided capable of imaging site of inflammation in a mammalian body, such peptides comprising a specific binding peptide comprising platelet factor 4 or peptide fragments thereof that bind to sites of inflammation, covalently linked to a radiolabel-binding moiety of formula Cp(aa)Cp      I.

wherein Cp is a protected cysteine residue and (aa) stands for an amino acid, and wherein the radiolabel-binding moiety is covalently linked to the specific binding peptides. In a preferred embodiment, the amino acid is glycine. In another preferred embodiment, the radiolabel-binding moiety is linked to the specific peptide via one or more amino acids.

In a second aspect, the present invention provides inflammation-imaging peptides that are covalently linked to a radiolabel-binding moiety having the following structure:

A—CZ(B)—[C($R^1R^2$)]$_n$—X      II.

wherein A is H, HOOC, $H_2$NOC, (peptide)-NHOC, (peptide)-OOC or $R^4$; B is H, SH or —$NHR^3$, —$N(R^3)$-(peptide) or $R^4$; X is SH or —$NHR^3$, —$N(R^3)$-(peptide) or $R^4$; $R^1$, $R^2$, $R^3$ and $R^4$ are independently H or straight or branched chain or cyclic lower alkyl; n is 0, 1 or 2; and: (1) where B is —$NHR^3$ or —$N(R^3)$-(peptide), X is SH and n is 1 or 2; (2) where X is —$NHR^3$ or —$N(R^3)$-(peptide), B is SH and n is 1 or 2; (3) where B is H or $R^4$, A is HOOC, $H_2$NOC, (peptide)-NHOC, (peptide)-OOC, X is SH and n is 0 or 1; (4) where A is H or $R^4$, then where B is SH, X is —$NHR^3$ or —$N(R^3)$-(peptide) and where X is SH, B is —$NHR^3$ or —$N(R^3)$-(peptide); (5) where X is H or $R^4$, A is HOOC, $H_2$NOC, (peptide)-NHOC, (peptide)-OOC and B is SH; (6) where Z is methyl, X is methyl, A is HOOC, $H_2$NOC, (peptide)-NHOC, (peptide)-OOC and B is SH and n is 0; and (7) where Z is SH and X is SH, n is not 0; and wherein the thiol moiety is in the reduced form.

In another embodiment, the invention provides radiolabeled inflammation-imaging reagents for imaging inflammatory sites within a mammalian body, comprising a specific binding peptide comprising platelet factor 4 or peptide fragments thereof, covalently linked to a radiolabel-binding moiety of formula:

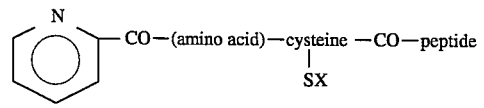

III.

[for purposes of this invention, radiolabel-binding moieties having this structure will be referred to as picolinic acid (Pic)-based moieties];

or

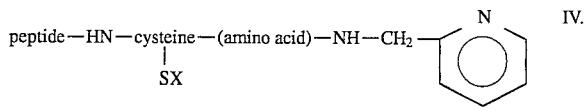

[for purposes of this invention, radiolabel-binding moieties having this structure will be referred to as picolylamine (Pica)-based moieties];
wherein X is H or a protecting group; (amino acid) is any amino acid; the radiolabel-binding moiety is covalently linked to the peptide and the complex of the radiolabel-binding moiety and the radiolabel is electrically neutral. In a preferred embodiment, the amino acid is glycine and X is an acetamidomethyl protecting group. In additional preferred embodiments, the peptide is covalently linked to the radiolabel-binding moiety via an amino acid, most preferably glycine, and the radiolabel is technetium-99m.

In yet another embodiment of the invention, a radiolabeled reagent is provided for imaging sites within a mammalian body, comprising a specific binding peptide and a bisamino bisthiol radiolabel-binding moiety covalently linked to the peptide. The bisamino bisthiol radiolabel-binding moiety in this embodiment of the invention has a formula selected from the group consisting of:

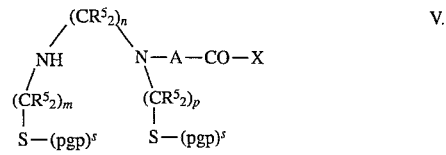

wherein each $R^5$ can be independently H, $CH_3$ or $C_2H_5$; each $(pgp)^S$ can be independently a thiol protecting group or H; m, n and p are independently 2 or 3; A is linear or cyclic lower alkyl, aryl, heterocyclyl, combinations or substituted derivatives thereof; and X is peptide;

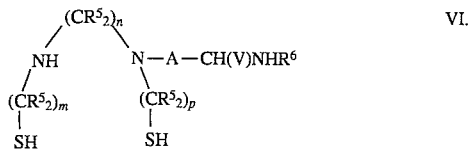

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-peptide; $R^6$ is H or peptide; provided that when V is H, $R^6$ is peptide and when $R^6$ is H, V is peptide. [For purposes of this invention, radiolabel-binding moieties having these structures will be referred to as "BAT" moieties]. In a preferred embodiment, the peptide is covalently linked to the radiolabel-binding moiety via an amino acid, most preferably glycine, and the radiolabel is technetium-99m.

The invention also comprises complexes of the peptides of the invention with Tc-99m, kits for preparing the peptides of the invention radiolabeled with Tc-99m, methods for radiolabeling the peptides of the invention with Tc-99m and methods for using the radiolabeled peptides of the invention for imaging sites of infection or inflammation in mammalian body by gamma scintigraphy.

The invention provides scintigraphic imaging agents that are complexes of the peptide reagents of the invention with Tc-99m and methods for radiolabeling the peptide reagents of the invention with Tc-99m. Radiolabeled complexes provided by the invention are formed by reacting the peptide reagents of the invention with Tc-99m in the presence of a reducing agent. Preferred reducing agents include but are not limited to dithionite ion, stannous ion and ferrous ion. Complexes of the invention are also formed by labeling the peptide reagents of the invention with Tc-99m by ligand exchange of a prereduced Tc-99m complex as provided herein.

The invention also provides kits for preparing scintigraphic imaging agents that are the peptide reagents of the invention radiolabeled with Tc-99m. Kits for labeling the peptide reagents of the invention with Tc-99m are comprised of a sealed vial containing a predetermined quantity of a peptide reagent of the invention and a sufficient amount of reducing agent to label the reagent with Tc-99m.

This invention provides methods for preparing peptide reagents of the invention by chemical synthesis in vitro. In a preferred embodiment, specific binding peptides are synthesized by solid phase peptide synthesis.

This invention provides methods for using scintigraphic imaging agents that are Tc-99m labeled peptide reagents for imaging sites of inflammation and infection within a mammalian body by obtaining in vivo gamma scintigraphic images. These methods comprise administering an effective diagnostic amount of Tc-99m labeled peptide reagents of the invention and detecting the gamma radiation emitted by the Tc-99m label localized at the inflammation site within the mammalian body.

The specific binding peptides of the invention may also be covalently linked to a polyvalent linking moiety. Polyvalent linking moieties of the invention are comprised of at least 2 identical linker functional groups capable of covalently bonding to specific binding peptides or Tc-99m binding moieties. Preferred linker functional groups are primary or secondary amines, hydroxyl groups, carboxylic acid groups or thiol-reactive groups. In preferred embodiments, the polyvalent linking moieties are comprised of bis-succinimdylmethylether (BSME), 4-(2,2-dimethylacetyl)benzoic acid (DMAB) and tris(succinimidylethyl)amine (TSEA).

Specific preferred embodiments of the present invention will become evident from the following more detailed description of certain preferred embodiments and the claims.

DETAILED DESCRIPTION OF THE INVENTION

The present invention provides Tc-99m labeled peptide reagents for imaging target sites within a mammalian body that specifically bind to sites of inflammation, the specific binding peptides being covalently linked to a radiolabel binding moiety wherein the radiolabel binding moiety binds a radioisotope.

The peptide reagents of this invention specifically bind to sites of inflammation. These reagents may also bind to leukocytes, preferably monocytes and neutrophils and most preferably to neutrophils. For purposes of this invention, the term "bind to leukocytes" is intended to mean that the specific binding peptides and peptide reagents of the present invention are capable of accumulating at sites of infection or inflammation in mammalian body sufficient to allow detection of the accumulation of radiolabeled complexes prepared from the reagents of the invention as disclosed herein at sites of infection or inflammation by gamma scintigraphy.

Preferred peptides of this invention include platelet factor 4 and peptides derived therefrom. For purposes of this invention, the term "peptides derived therefrom" is intended to encompass peptides having an amino acid sequence homologous to all or a portion of the platelet factor 4 amino acid sequence. Also intended to be circumscribed by this term are peptide fragments of platelet factor 4, whether generated by proteolytic degradation of native platelet factor 4 protein or by chemical synthesis of a portion of the platelet factor 4 amino acid sequence. Peptide fragments useful in the practice of this invention include those fragments capable of specifically binding to sites of infection and inflammation in a mammalian body. Examples of such peptides are presented hereinafter in the Examples.

In Cp(aa)Cp-containing peptides, the Cp is a protected cysteine where the S-protecting groups are the same or different and may be but not limited to:

—$CH_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—$CH_2$-(4-methoxyphenyl);

—CH-(4-pyridyl)(phenyl)$_2$;

—C($CH_3$)$_3$-9-phenylfluorenyl;

—$C_2$NHCOR (R is unsubstituted or substituted alkyl or aryl);

—$CH_2$—NHCOOR (R is unsubstituted or substituted alkyl or aryl);

—CONHR (R is unsubstituted or substituted alkyl or aryl);

—$CH_2$—S—$CH_2$-phenyl.

Radiolabel binding moieties comprising cysteine-sulfur protecting groups designated "(pgp)$^S$", such as the bisamino, bisthiol moieties of the invention, are also described by the above-mentioned listing of protecting groups.

The preferred protecting group has the formula —$CH_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

Peptides of the present invention may be chemically synthesized in vitro. Peptides of the present invention can generally advantageously be prepared on a peptide synthesizer. The peptides of this invention can be synthesized wherein the radiolabel binding moiety is covalently linked to the peptide during chemical in vitro synthesis, using techniques well known to those with skill in the art. Such peptides covalently-linked to the radiolabel binding moiety upon synthesis are advantageous because specific sites of covalent linkage can be determined therein.

Radiolabel binding moieties of the invention may be introduced into the target specific peptide during peptide synthesis. For embodiments [e.g., Pic-Gly-Cys(protecting group)-] comprising picolinic acid (Pic-), the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- chelator are provided in the Examples hereinbelow. This invention provides for the incorporation of these chelators into virtually any platelet factor 4-derived peptide, resulting in a Tc-99m radiolabeled peptide.

This invention also provides specific-binding small synthetic peptides which incorporate bisamine bisthiol (BAT) chelators which may be labeled with Tc-99m.

In forming a complex of radioactive technetium with the peptide reagents of this invention, the technetium complex, preferably a salt of Tc-99m pertechnetate, is reacted with the peptide reagents of this invention in the presence of a reducing agent; in a preferred embodiment, the reducing agent is stannous chloride. Complexes and means for preparing such complexes are conveniently provided in a kit form comprising a sealed vial containing a predetermined quantity of the peptide reagent of the invention that are to be labeled and a sufficient amount of reducing agent to label the reagent with Tc-99m. Alternatively, the complex may be formed by reacting the peptide reagents of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. The reaction of the peptide reagents of this invention with Tc-pertechnetate or preformed Tc-99m labile complex can be carried out in an aqueous medium at room temperature. When an anionic complex is formed in an aqueous medium, the radiolabeled complex is in the form of a salt with a suitable cation such as sodium cation, ammonium cation, mono, di- or tri-lower alkyl amine cation, or any pharmaceutically acceptable cation.

In a preferred embodiment of the invention, a kit for preparing technetium-labeled peptides is provided. The peptide reagents of the invention can be chemically synthesized using methods and means well-known to those with skill in the art and described hereinbelow. Peptides are covalently linked to a radiolabel binding moitey wherein the radiolabel binding moiety binds a radioisotope. An appropriate amount of the peptide reagent is introduced into a vial containing a reducing agent, such as stannous chloride or a solid-phase reducing agent, in an amount sufficient to label the reagent with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 2 hereinbelow.

Radioactively labeled peptide reagents provided by the present invention are provided having a suitable amount of radioactivity. In forming the Tc-99m radioactive complexes, it is generally preferred to form radioactive complexes in solutions containing radioactivity at concentrations of from about 0.01 millicurie (mCi) to 100 mCi per ml.

Technetium-labeled peptide reagents provided by the present invention can be used for visualizing sites of inflammation, including abscesses and sites of "occult" infection. The Tc-99m labeled peptides provided by the present invention can also be used for visualizing sites of inflammation caused by tissue ischemia, including such disorders as inflammatory bowel disease and arthritis. In accordance with this invention, the technetium-labeled peptides or complexes either as a complex or as a salt with a pharmaceutically acceptable counterion are administered in a single unit injectable dose. Any of the common carders known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) resin for carboxyl-terminus acids or Rink amide resin for carboxyl-terminus amides. Where appropriate N-α-acetyl groups were introduced by treating the resin-bound peptide with acetic anhydride in N-methylpyrrolidinone (NMP). Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Tc-99m

Peptide (0.1 mg) prepared as in Example 1 was dissolved in 0.1 mL of 0.05M potassium phosphate buffer (pH 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 µL of Tc-99m gluceptate was then added to the peptide reagent and the reaction allowed to proceed at 100° C. or at room temperature for 30 min and then filtered through a 0.2 µm filter.

The purity of the Tc-99m labeled peptide reagent was determined by HPLC using a Vydak 218TP54 analytical column (RP-18, 5 micron, 220×4.6 mm) and eluted as described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

| Peptides | SEQ ID# | FABMS MH$^+$ | Radiochemical Yield | HPLC R$_t$ (min) |
|---|---|---|---|---|
| C$_{Mob}$GC$_{Acm}$PLYKKIIKKLLES | 1 | 2028 | 97% | Bound |
| [DTPA]C$_{Acm}$GC$_{Acm}$PLYKKIIKKLLES | 2 | 2468 | 91% | 11.6 |
| PicGC$_{Acm}$PLYKKIIKKLLES | 3 | 1910 | 81% | 12.9, 13.3 |
| C$_{Acm}$GC$_{Acm}$PLYKKIIKKLLES | 4 | 2093 | 96% | 12.6 |
| (AcCC$_{Acm}$GC$_{Acm}$PLYKKIIKKLLES)$_2$BSME | | 4483 | 97% | 11.6 |

-continued

| Peptides | SEQ ID# | FABMS MH+ | Radiochemical Yield | HPLC $R_t$ (min) |
|---|---|---|---|---|
| AcKKKKKC$_{Acm}$GC$_{Acm}$GGPLYKKIIKKLLES | 5 | 2276 | 98% | 11.3 |
| [BAT]GGPLYKKIIKKLLES | 6 | 2006 | 91% | 9.5 |
| (AcCKKC$_{Acm}$GC$_{Acm}$PLYKKIIKKLLES)$_2$BSME | | N.D. | N.D. | N.D. |

Ac = acetyl;
Pic = picolinoyl (pyridine-2-carbonyl);
Acm = acetamidomethyl;
Mob = 4-Methoxybenzyl;
[DTPA] = diethylenetriaminepentaacetic acid;
BSME = bis-succinimidylmethyl ether HPLC methods:
general: solvent A=0.1% CF3COOH/H2O
solvent $B_{90}$=0.1% $CF_3COOH$/90% $CH_3CN$/$H_2O$
solvent flow rate=1 ml/min
Vydak column=Vydak 218TP54 RP-18, 5μ×220 mm×4.6 mm analytical column with guard column Method: Vydak column 100% A to 100% $B_{90}$ in 10 min It should be understood that the foregoing disclosure emphasizes certain specific embodiments of the invention and that all modifications or alternatives equivalent thereto are within the spirit and scope of the invention as set forth in the appended claims.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1..3
( D ) OTHER INFORMATION: /label=Tc- 99m-chelator
/ note="The sidechain sulfur atom of the Cys at position 1 is protected by a 4-methoxybenzyl group, and the sidechain sulfur atom of the Cys at position 3 is protected by an acetamidomethyl group"

( x i ) SEQUENCE DESCRIPTION: SEQ ID NO:1:

Cys Gly Cys Pro Leu Tyr Lys Lys Ile Ile Lys Lys Leu Leu Glu Ser
1               5                   10                  15

( 2 ) INFORMATION FOR SEQ ID NO:2:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1..3
( D ) OTHER INFORMATION: /label=Tc- 99m-chelator
/ note="The sidechain sulfur atoms of both Cys residues are each protected by an acetamidomethyl group, and a diethylenetriaminepentaacetic acid group is covalently linked to the N-terminal amino group"

( x i ) SEQUENCE DESCRIPTION: SEQ ID NO:2:

Cys Gly Cys Pro Leu Tyr Lys Lys Ile Ile Lys Lys Leu Leu Glu Ser (2) INFORMATION FOR SEQ ID NO:3:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..2
        (D) OTHER INFORMATION: /label=Tc-99m-chelator
            / note="The sidechain sulfur atom of the Cys
            residue is protected by an acetamidomethyl group,
            and a (pyridine-2-carbonyl) group is covalently
            linked to the N-terminal amino group"

(xi) SEQUENCE DESCRIPTION: SEQ ID NO:3:

```
Gly Cys Pro Leu Tyr Lys Lys Ile Ile Lys Lys Leu Leu Glu Ser
 1               5                  10                  15
```

(2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label=Tc-99m-chelator
            / note="The sidechain sulfur atoms of both Cys
            residues are each protected with an
            acetamidomethyl group"

(xi) SEQUENCE DESCRIPTION: SEQ ID NO:4:

```
Cys Gly Cys Gly Gly Pro Leu Tyr Lys Lys Ile Ile Lys Lys Leu Leu
 1               5                  10                  15
Glu Ser
```

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..8
        (D) OTHER INFORMATION: /label=Tc-99m-chelator
            / note="The N-terminal amino group is acetylated,
            and the sidechain sulfur atoms of both Cys
            residues are each protected by an acetamidomethyl
            group"

(xi) SEQUENCE DESCRIPTION: SEQ ID NO:5:

```
Lys Lys Lys Lys Lys Cys Gly Cys Pro Leu Tyr Lys Lys Ile Ile Lys
 1               5                  10                  15
Lys Leu Leu Glu Ser
                 20
```

(2) INFORMATION FOR SEQ ID NO:6:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1..2
    (D) OTHER INFORMATION: /label=Tc- 99m-chelator
        / note="A bis-amino, bis-thiol Tc-99m chelator
        [BAT]is covalently attached to the N-terminal
        amino group"

(xi) SEQUENCE DESCRIPTION: SEQ ID NO:6:

Gly Gly Pro Leu Tyr Lys Lys Ile Ile Lys Lys Leu Leu Glu Ser
1               5                   10                  15

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:7:

Pro Leu Tyr Lys Lys Ile Ile Lys Lys Leu Leu Glu Ser
1               5                   10

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:8:

Lys Lys Ile Ile Lys Lys Leu Leu Glu Ser
1               5                   10

---

What is claimed is:

1. A reagent for preparing a technetium-99m (Tc-99m) radiolabeled peptide for imaging sites of inflammation within a mammalian body, comprising a specific binding peptide comprising platelet factor 4 or peptide fragments thereof wherein the peptide specifically binds to sites of inflammation, covalently linked to a Tc-99m binding moiety.

2. A reagent for preparing a technetium-99m (Tc-99m) radiolabeled peptide for imaging sites of inflammation within a mammalian body, comprising a specific binding peptide comprising platelet factor 4 or peptide fragments thereof wherein the peptide specifically binds to sites of inflammation, covalently linked to a Tc-99m binding moiety of formula selected from the group consisting of:

$$Cp(aa)Cp \quad \text{I.}$$

wherein Cp is a protected cysteine and (aa) is an amino acid;

$$A-CZ(B)-\{C(R^1R^2)\}_n-X \quad \text{II.}$$

wherein

A is H, HOOC, $H_2$NOC, (peptide)-NHOC, (peptide)-OOC or $R^4$;

B is H, SH, —$NHR^3$, —$N(R^3)$-(peptide), or $R^4$;

X is H, SH, —$NHR^3$, —$N(R^3)$-(peptide) or $R^4$;

Z is H or $R^4$;

$R^1$, $R^2$, $R^3$ and $R^4$ are independently H or lower straight or branched chain or cyclic alkyl;

n is 0, 1 or 2;

and where B is —$NHR^3$ or —$N(R^3)$-(peptide), X is SH, and n is 1 or 2;

where X is —$NHR^3$ or —$N(R^3)$-(peptide), B is SH, and n is 1 or 2;

where B is H or $R^4$, A is HOOC, $H_2$NOC, (peptide)-NHOC, (peptide)-OOC, X is SH, and n is 0 or 1;

where A is H or $R^4$, then where B is SH, X is —$NHR^3$ or —$N(R^3)$-(peptide) and where X is SH, B is —$NHR^3$ or —$N(R^3)$-(peptide);

where X is H or $R^4$, A is HOOC, $H_2$NOC, (peptide)-NHOC, (peptide)-OOC and B is SH;

where Z is methyl, X is methyl, A is HOOC, $H_2$NOC, (peptide)-NHOC, (peptide)-OOC, B is SH and n is 0;

where B is SH and X is SH, n is not 0;

and wherein the thiol moiety is in the reduced form; and

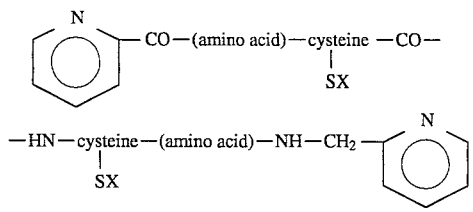

wherein

X=H or a protecting group;

(amino acid)=any amino acid;

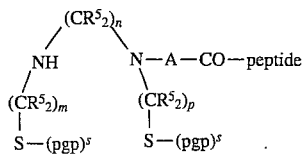

wherein each $R^5$ is independently H, $CH_3$ or $C_2H_5$;

each $(pgp)^5$ is independently a thiol protecting group or H;

m, n and p are independently 2 or 3;

A=linear or cyclic lower alkyl, aryl, heterocyclyl, combinations or substituted derivatives thereof;

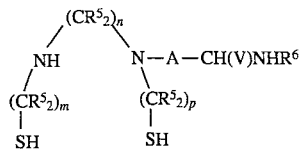

wherein each $R^5$ is independently H, lower alkyl having 1 to 6 carbon atoms, phenyl, or phenyl substituted with lower alkyl or lower alkoxy;

m, n and p are independently 1 or 2;

A=linear or cyclic lower alkyl, aryl, heterocyclyl, combinations or substituted derivatives thereof;

V=H or —CO-peptide;

$R^6$=H or peptide;

and wherein when V=H, $R^6$=peptide and when $R^6$=H, V=—CO-peptide;

wherein the radiolabel-binding moiety forms a complex with a radioisotope and the complex is electrically neutral.

3. The reagent of claim 2 wherein the specific binding peptide and Tc-99m binding moiety are covalently linked through one or more amino acids.

4. The reagent of claim 2 wherein the protected cysteine of the Tc-99m binding moiety having formula I has a protecting group of the formula

wherein R is a lower alkyl having 1 to 6 carbon atoms, 2-,3-,4-pyridyl, phenyl, or phenyl substituted with lower alkyl, hydroxy, lower alkoxy, carboxy, or lower alkoxycarbonyl.

5. The reagent of claim 2 wherein the Tc-99m binding moiety of formula Cp(aa)Cp has the formula:

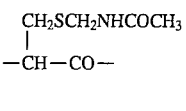

6. The reagent according to claim 2 wherein the Tc-99m binding moiety is bound to Tc-99m.

7. The reagent of claim 2 wherein the specific binding peptide is selected from the group consisting of peptides having the amino acid sequence PLYKKIIKKLLES (SEQ ID NO.:7) and KKIIKKLLES (SEQ ID No.:8).

8. The reagent of claim 1 wherein the reagent further comprises a polyvalent linking moiety covalently linked to a multiplicity of specific binding peptides and also covalently linked to a multiplicity of radiolabel-binding moieties to comprise a multimeric polyvalent scintigraphic imaging agent, wherein the molecular weight of the multimeric polyvalent scintigraphic imaging agent is less than about 20,000 daltons.

9. The reagent of claim 8 that is a multimeric polyvalent scintigraphic imaging agent, wherein the polyvalent linking moiety is bis-succinimidylmethylether, 4-(2,2-dimethylacetyl)benzoic acid, diethylenetriaminepentaacetic acid, tris(succinimidylethyl)amine or a derivative thereof.

10. A complex formed by reacting the reagent of claim 2 with technetium-99m in the presence of a reducing agent.

11. The complex of claim 10, wherein the reducing agent is selected from the group of a dithionite ion, a stannous ion, or a ferrous ion.

12. A complex formed by labeling the reagent of claim 2 with technetium-99m by ligand exchange of a prereduced technetium-99m complex.

13. A kit for preparing a radiopharmaceutical preparation, said kit comprising sealed vial containing a predetermined quantity of the reagent of claim 2 and a sufficient amount of reducing agent to label the reagent with technetium-99m.

14. The process of preparing the reagent according to claim 2 wherein the reagent is chemically synthesized in vitro.

15. The process of preparing the reagent according to claim 14 wherein the specific binding peptide is synthesized by solid phase peptide synthesis.

16. The reagent according to claim 2 wherein the radiolabel binding moiety is covalently linked to the specific binding peptide during in vitro chemical synthesis.

17. The reagent according to claim 16 wherein the radiolabel binding moiety is covalently linked to the specific binding peptide during solid phase peptide synthesis.

18. A method for labeling a peptide according to claim 2 comprising reacting the peptide with Tc-99m in the presence of a reducing agent.

19. The method of claim 18, wherein the reducing agent is selected from the group of a dithionite ion, a stannous ion, or a ferrous ion.

20. A composition of matter comprising the reagent of claim 2 having the formula:

21. A composition of matter having the formula:

Acetyl-NHCHCO.—Cys(Acm)—Gly—Cys(Acm)—Pro—Leu—Tyr—Lys—Lys—Ile—Ile—Lys—Lys—Leu—Leu—Glu—Ser.

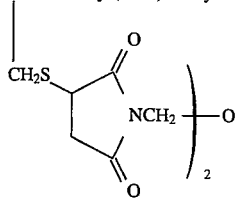

22. A composition of matter comprising the reagent of claim 2 having the formula:

AcKKKKKC$_{Acm}$GC$_{Acm}$GGPLYKKIIKKLLES (SEQ ID No.:5).

23. A composition of matter comprising the reagent of claim 2 having the formula:

C$_{Mob}$GC$_{Acm}$PLYKKIIKKLLES (SEQ ID No.:1).

24. A composition of matter comprising the reagent of claim 2 having the formula:

C$_{Acm}$GC$_{Acm}$PLYKKIIKKLLES (SEQ ID No.:2).

25. A composition of matter comprising the reagent of claim 2 having the formula:

PicGC$_{Acm}$PLYKKIIKKLLES (SEQ ID No.:3).

26. A composition of matter comprising the reagent of claim 2 having the formula:

GGPLYKKIIKKLLES (SEQ ID No.:6).

27. A composition of matter having the formula:

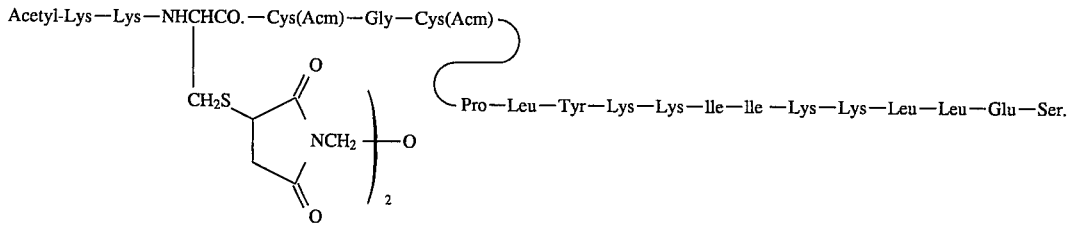

* * * * *